Figure 1:
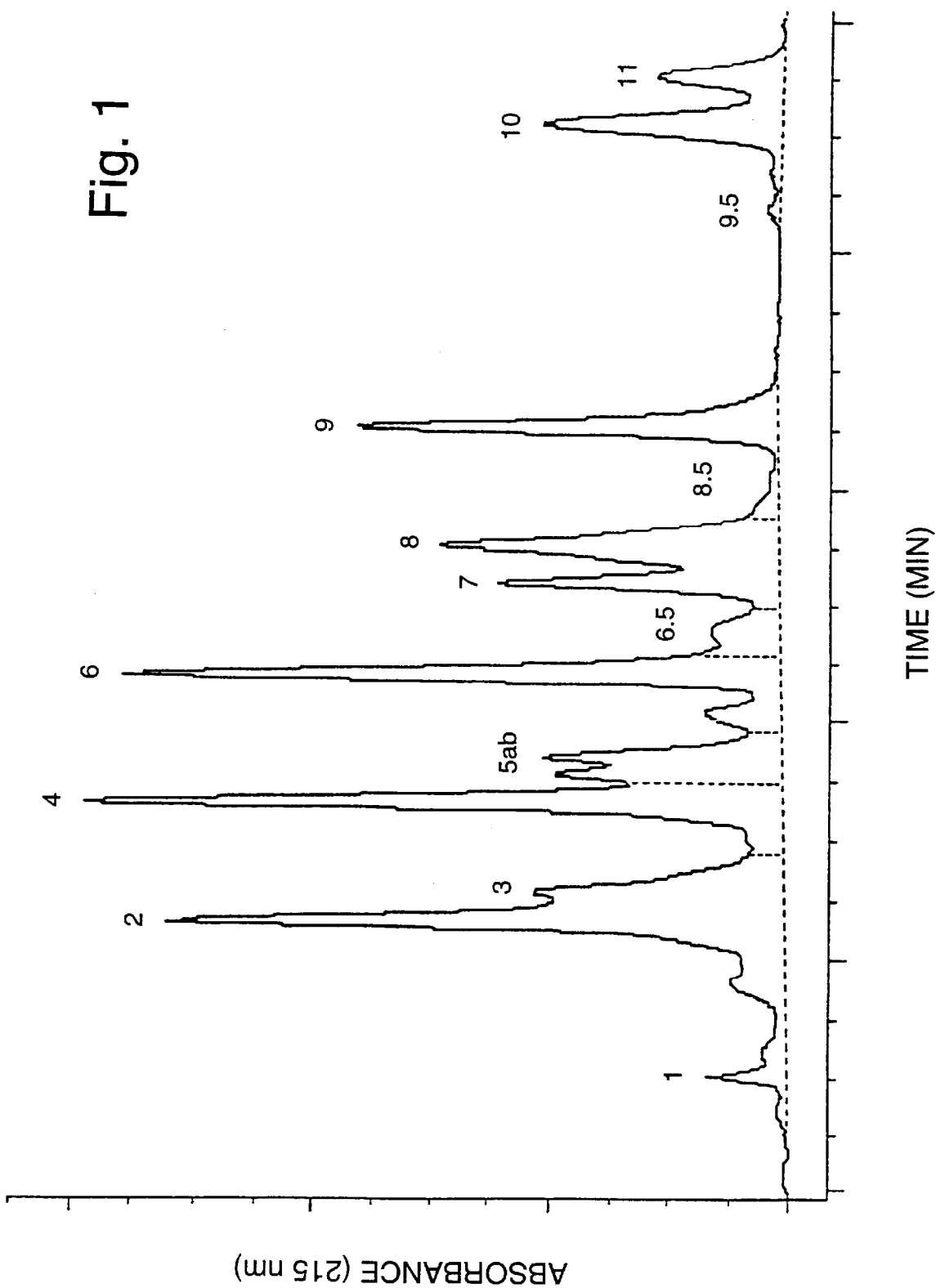

United States Patent [19]

Everett et al.

[11] Patent Number: 5,821,080

[45] Date of Patent: Oct. 13, 1998

[54] CELL LINE

[75] Inventors: Peter Anthony Everett; Brendan Patrick Hughes, both of Kent, United Kingdom; Cornelia Rossman, Lund, Sweden

[73] Assignee: Glaxo Wellcome Inc., Research Triangle Park, N.C.

[21] Appl. No.: 624,428

[22] PCT Filed: Dec. 11, 1995

[86] PCT No.: PCT/GB95/02874

§ 371 Date: Jun. 27, 1996

§ 102(e) Date: Jun. 27, 1996

[87] PCT Pub. No.: WO97/44440

PCT Pub. Date: Nov. 27, 1997

[30] Foreign Application Priority Data

Dec. 9, 1994 [GB] United Kingdom .................. 9425050

[51] Int. Cl.$^6$ .................. C12P 21/02; C12N 5/10
[52] U.S. Cl. .................. 435/69.1; 435/69.51; 435/172.3; 435/235.1; 435/372
[58] Field of Search .................. 435/240.2, 69.1, 435/69.51, 235.1, 372

[56] References Cited

PUBLICATIONS

Middleton et al., *Int. J. Cancer*, vol. 52, 1992, 451–454 1992.

*Primary Examiner*—James Ketter
*Attorney, Agent, or Firm*—Nixon & Vanderhye

[57] ABSTRACT

A Namalwa cell line which is free of squirrel monkey retrovirus is useful for alpha-interferon production. The cell line can be used for the expression of recombinant polypeptides. It can be employed for packaging viruses for use in gene therapy.

14 Claims, 2 Drawing Sheets

CELL LINE

The present invention relates to Namalwa cell lines and their use.

Human alpha-interferons (α-IFNs) belong to a multigene family located on a 400 kb segment of human chromosome 9. The family comprises at least 13 genes encoding α-IFN subtypes. Each α-IFN protein consists of 165 or 166 amino acid residues with molecular weights of between 18 and 26 kD (depending on the degree of glycosylation). Although chemically distinct, the subtypes are closely related with regions of highly conserved amino acid sequences.

One commercially available source of α-IFN is human lymphoblastoid alpha nl IFN (α n1 IFN). Which is a natural α-IFN. It is produced by stimulating a Namalwa human lymphoblastoid cell line with Sendai virus to produce a mixture of at least 13 subtypes of α-IFN, which are then purified by chromatography (U.S. Pat. No. 4,216,203; EP-A-0000520; EP-A-0097353). The number and quantity of particular subtypes is kept within defined limits during the manufacturing process.

This technique for producing α-IFN was in fact developed in the early 1970's. It was during that period that the cell-line now used to produce all currently commercially available human lyphoblastoid interferon was generated from a Burkitt's lymphoma tumour. This tumour was removed from a single individual named Namalwa, thus generating the eponymously titled cell line (Strander H. et al, J. Clin. Microbiol. 1, 116–117, 1975 and Christofinis G. J. et al, J. Gen. Virol. 52, 169–171, 1981). Namalwa cells are publicly available under ATCC Deposit No. 00001432-CRL.

Namalwa cells have also been used for the preparation of recombinant proteins (Yanagi H. et al, Gene 76, 19–26, 1989 and Okamoto M. et al, Bio/Technology 550–553, 1990). Namalwa cells are attractive for the production of recombinant proteins of human origin. Correct post-translational processing of the recombinant human proteins can be expected. Further, industrial-scale production of Namalwa cell lines is well-established because of their use for producing α-IFN.

The possibility that there may be contaminants associated with products obtained from a Namalwa cell line has been extensively researched. Namalwa cells have been tested for contamination with bacteria, viruses and mycoplasma. Some level of Epstein-Barr virus (EBV) have been detected. Infectious virus is not formed, though. Further, EBV early antigen cannot be detected even when cells are treated with chemicals such as bromodeoxyuridine which can induce EBV replication.

However, the presence of genome of the squirrel monkey retrovirus (SMRV, a type D retrovirus) has been detected (Middleton et al, Int. J. Cancer 52, 451–454, 1992). SMRV was first isolated from a squirrel monkey lung culture and displays an extended host range in vitro including canine, human, chimpanzee, rhesus monkey and mink cells. The virus is of particular interest since it has been identified as a contaminant of a number of cell lines. To date, two strains of the virus, SMRV and SMRV-H, have been identified on the basis of differences in restriction endonuclease patterns and sequence variation.

It is possible to ensure that no viable SMRV particles survive the production protocols that are employed to obtain products using Namalwa cell lines. However, it is clearly preferable that no SMRV genome should be present in Namalwa cells. SMRV genomes were detected by Middleton et al (supra) in all eight of a random selection of eight Namalwa cell-lines sampled from laboratories world-wide. Hence it is considered likely that all prior, publicly available, Namalwa cells contain the SMRV genome.

Conclusively proving that particular cells are lacking a viral contaminant is clearly dependent upon the sensitivity of the particular assay system employed. Direct assay for the presence of viral DNA by techniques such as the polymerase chain reaction (PCR) may allow sensitivities of detection of up to one viral genome per 100 to 1000 cells, even up to one viral genome per 1000 cells. If however a new cell-line is cloned from a single cell, this will of necessity contain either one or more viral genome per cell or none. Consequently the possibility of obtaining a false negative assay result will be much lower for such a cloned cell-line than for genetically heterogeneous cells.

Prior to the present invention, it was considered that the presence of SMRV was an inherent characteristic of a Namalwa cell line. As mentioned above, it is considered likely that all prior, publically available, Namalwa cell lines contain the SMRV genome.

Unexpectedly, we have located a SMRV-free Namalwa cell line. We also unexpectedly found that Namalwa cell lines could be cloned successfully by using high density, rather than low density, static cultures. The resulting cloned Namalwa cell lines were shown to be SMRV-free. Each cloned cell line had been derived from a single cell, thus providing a guarantee that the entire cell population of the cloned cell line was SMRV-free.

Accordingly, the present invention provides a Namalwa cell line which is SMRV-free. Typically, the cell line is capable of producing a heterogenous population of α-IFN sub-types.

The cell line is preferably a cloned cell line. In that event, the α-IFN sub-types are generally substantially the same as those produced by existing Namalwa cell lines that are used for the production of commercially available lymphoblastoid interferon. A cloned cell-line of the present invention is a genetically uniform population of cells derived from a single cell and is a clone notwithstanding the occurrence of any random mutation during the generation of the clonal population from its single parent cell.

Preferably the α-IFN sub-types generated by a cell line of the present invention contain at least α-IFN sub-types 2b, 7, 10, 17 and 21; more preferably 1, 2b, 5, 7, 8, 10, 14, 17 and 21. The α-IFN sub-types are advantageously produced in the relative quantitative ranges indicated in Table 1 below. These ranges define the limits within which the subtypes of therapeutically acceptable lymphoblastoid interferon preferably fall. It is most preferred that a cell line generates an α-IFN sub-type profile substantially equivalent to that produced by the Namalwa cells used for the production of Wellferon, for example by the cells forming the subject of ATCC Deposit No. 00001432-CRL. This deposit was made at ATCC, Rockville, Md. 20852, USA on 7th Jul. 1978.

TABLE 1

| Sub-type | % by weight |
| --- | --- |
| 1 | 1–16 |
| 2b | 19–37 |
| 5 | 4–13 |
| 7 + 17 | 11–20 |
| 8 | 2–14 |
| 10 | 8–21 |
| 14 | 2–13 |
| 21 | 8–20 |

Two SMRV-negative cell lines in accordance with the present invention have been made the subject of Budapest Treaty deposits at the European Collection of Animal Cell Cultures, Porton Down, Salisbury SP4 0JG, GB on 8th Dec. 1994 under accession nos. ECACC 94120840 and ECACC 94120841. Those two deposited cell lines and cell lines derived therefrom are particularly preferred embodiments of the invention. Progeny of the deposited cell lines thus form an aspect of the invention.

Useful cell lines according to the invention are SMRV-free cell lines capable of producing a heterogeneous population of α-IFN sub-types, which sub-types are substantially the same as those produced by either of deposited cell lines nos. ECACC 94120840 and ECACC 94120841. The population of sub-types, the IFN sub-type profile, may be substantially the same as that produced by either of these two cell lines. The relative proportions of each α-IFN sub-type may thus be substantially the same as the relative proportions of each sub-type produced by either of the deposited cell lines.

We fortuitously located a SMRV-negative Namalwa cell line. The cell line of the invention may thus be a naturally-occurring SMRV-free Namalwa cell line. Such a cell line may be in isolated form. The cell line may have been cloned.

A cloned cell line of the invention can be prepared by a novel form of double limiting dilution cloning. Contrary to known dilution cloning methodologies, it was discovered that, when cells of suitable viability were subsequently plated out in wells to obtain single colonies, advantageous results were obtained by using high density (rather than the expected low density) static cultures.

It is preferable to perform a double round of dilution cloning when generating a cloned cell line in order to obtain a very high statistical probability of up to 99.99% that the resultant cell line originates from a single cell. Parental SMRV-free Namalwa cells are grown in static culture to high density in an appropriate medium containing a suitable antibiotic, split, diluted down and regrown to high density, discarding those cultures not demonstrating >90% viability using a viability assay such as trypan blue exclusion. The cells are then split and diluted down again.

The cell density should preferably be $1.8 \times 10^6$ cells $ml^{-1}$ or more, for example from $1.8 \times 10^6$ to $2.4 \times 10^6$ cells $ml^{-1}$ or from $2.0 \times 10^6$ to $2.2 \times 10^6$ cells $ml^{-1}$. A suitable cell density is therefore approximately 2 million cells $ml^{-1}$. Dilution down to 0.2 million cells $ml^{-1}$ is suitable.

However, a SMRV-negative Namalwa cell culture may be generated from a SMRV-positive Namalwa cell line by using recombinant DNA technology. Thus, methods such as directed homologous recombination can be used to recombine out the integrated SMRV genome and replace it with a piece of non-coding DNA.

Deletion of the SMRV genome from the relevant chromosome of a SMRV-positive Namalwa cell line is thus possible. The sequences flanking the SMRV genome are identified. A vector is constructed which contains at least 3 kb of the flanking sequence to either side of the SMRV genome. A targeting construct is made in which the region to be deleted is replaced by a positive selectable marker such as one encoding drug resistance, leaving the flanking DNA unaltered.

This construct, typically a plasmid, is then linearized and introduced into the target SMRV-positive cells. Recombination occurs as a low frequency natural event, and cells in which this has been successful can be selected by their ability to grow in the drug which should have been introduced by the targeting construct. Resistant clones must then be analysed to ensure that drug resistance has not occurred by a non-specific mechanism, and that the SMRV genome has been successfully deleted. It is possible to engineer the targeting construct in such a way as to select against non-specific recombinants.

Once this has been completed one copy of the genome has been deleted. In a heterozygous organism the second copy must also be removed. This is done by the same procedure, with a targeting construct that may be identical to the first one in all aspects, except that it contains a different drug resistant selectable marker. Double recombinants can then be selected that are resistant to both drugs, due to integration into both chromosomes.

Alternatively, it is possible that a sub-population of SMRV-free cells may exist in a SMRV-positive Namalwa cell line. A SMRV-positive Namalwa cell line could thus be cloned. Clones of SMRV-free cells could then be identified. The double limiting dilution cloning procedure above can be employed.

The present invention also provides a process for producing alpha-interferon, which process comprises culturing a cell-line of the present invention and isolating the alpha-interferon thus produced. A heterologous population of α-IFNs is thus obtained. Cell-lines of the present invention may be cultured according to any appropriate method. An interferon inducer such as Sendai virus may be added to the culture. The alpha-interferon may be isolated by affinity chromatography using anti-IFN antibodies. A suitable polyclonal antibody for use in such generation may be produced by techniques well known in the art (U.S. Pat. No. 4,216, 203).

In more detail, a sample of a Namalwa cell line according to the invention may be thawed from storage in liquid nitrogen and grown in cultures of increasing size leading up to large scale culture. A suitable culture medium may include RPMI 1640 supplemented with serum, such as gamma irradiated adult bovine serum. When the cell population is optimal, sodium butyrate may be added to slow the growth rate of the cells and optimise the subsequent IFN yield (U.S. Pat. No. 4,216,203). The cells should then be induced to produce IFN, typically by the addition of Sendai virus. The crude α-IFN is isolated and then passed through a purification procedure involving precipitations, solvent extraction and chromatography. The final form has a purity of at least 95% and a specific activity of approximately 100 IU/mg protein and consists of at least 13 different subtypes of α-IFN (Finter N. B. et al, CSHSQB 101, 571–575, 1986).

Pharmaceutical formulations of the present invention comprise α-IFN produced from cell lines of the present invention in admixture with a pharmaceutically acceptable carrier. Preferably the carrier comprises a mixture of sodium chloride, tris (Trimethamine US), glycine and human albumin solution. More preferably the sodium chloride is present at 8.5 mg $ml^{-1}$, the Tris at 1.21 mg $ml^{-1}$, the glycine at 0.75 mg $ml^{-1}$ and the human serum albumin at a concentration resulting in a final protein concentration in the formulation of 1.5 mg $ml^{-1}$.

α-IFNs produced from cell lines of the present invention may be used in the therapy of any known lymphoblastoid IFN-responsive condition and may be administered by routes and in quantities well known in the art and substantially identical to those known for existing commercial therapeutic lymphoblastoid IFNs.

For example in the treatment of hairy cell leukaemia, a dosing regime of three megaunits (3 MU) should be administered e.g. intravenously (iv) daily for between 12 and 16 weeks followed by 3 MU three times per week until no hairy cells are detectable in the bone marrow. In hepatitis B therapy, 10–15 MU may be administered three times weekly for between 4 and 6 months while, for hepatitis C, 3 MU may be administered for up to 6 months. These dosing regimes are accepted in the art but do not preclude the use of alternative or higher dosing regimes should the particular clinical factors dictate it.

A cell line of the invention can also be used as an expression system within which recombinant proteins may be produced. Accordingly, the present invention provides:

- a cell line according to the invention which harbours an exogenous expressible DNA sequence encoding a polypeptide of interest;
- a process for the preparation of such a cell line, which process comprises transfecting a cell line according to the invention with an expressible DNA sequence encoding the polypeptide of interest; and
- a process for the preparation of a polypeptide of interest, which process comprises maintaining a cell line harbouring an exogenous expressible DNA sequence encoding the polypeptide of interest under such conditions that the polypeptide is expressed and recovering the expressed polypeptide.

A cell line capable of expressing a polypeptide of interest can be prepared utilising an expression vector which comprises a DNA sequence encoding the polypeptide. The polypeptide is typically a human polypeptide, for example a growth factor. The polypeptide may be insulin, erythropoietin, human growth hormone, GCSF, GMCSF, tissue plasminogen activator, urokinase, blood factor VIII, protein C, etc.

The expression vector is capable of expressing the polypeptide of interest when provided in SMRV-free cells according to the invention. Appropriate transcriptional and translational control elements are provided, including a promoter operably linked to the DNA sequence encoding the desired polypeptide. The promoter may be the SV40 (simian virus 40) early promoter. An enhancer, a transcriptional termination site and translational stop and start codons are provided. A suitable splice junction and a polyadenylation site may be present. The DNA sequence is provided in the correct frame such as to enable expression of the polypeptide to occur.

The expression vector is thus a vector which is compatible with the SMRV-free Namalwa cells. If desired, a selectable marker gene is present. The expression vector is typically a plasmid. It generally comprises an origin of replication.

SMRV-free Namalwa cells are transfected with the expression vector. The transfected cells are then maintained under conditions which enable expression of the desired polypeptide to occur. The transfected cells are cultured in an appropriate medium for this purpose. The desired polypeptide that has been expressed is isolated. The polypeptide is purified as required.

The SMRV-free cell lines of the invention can further be used as a packaging/growth complementing cell line for viruses, for example retroviruses or adenoviruses. Accordingly, the present invention provides:

- a cell line according to the invention which harbours sufficient expressible viral genes to enable a corresponding viral vector comprising replication signals, a packaging sequence and a gene of interest to be packaged therein;
- a process for the preparation of such a cell line, which process comprises transfecting a cell line according to the invention with sufficient expressible viral genes to enable a corresponding viral vector comprising replication signals, a packaging sequence and a gene of interest to be packaged therein; and
- a process for packaging viruses, which process comprises transfecting a cell line which harbours sufficient expressible viral genes to enable a corresponding viral vector comprising replication signals, a packaging sequence and a gene of interest to be packaged therein with the said viral vector and recovering the resulting packaged virus.

The packaged viruses can be used in gene therapy. These viruses are unable to replicate autonomously within a target cell but can deliver a desired gene to that cell.

The desired gene is initially provided in a viral vector which additionally comprises the viral replication signals and a packaging sequence, sometimes called the psi packaging sequence or an encapsidation sequence. The viral vector thus lacks, at least, functional sequences which are necessary for replication of the virus within an infected cell.

The cell line may be employed for packaging a retrovirus, in which case the viral vector is a retroviral vector. Suitable retroviruses which may be packaged include murine leukemia virus (MLV), gibbon ape leukemia virus (GALV), reticuloendothelial virus (REV), spleen necrosis virus (SNV, mammalian C type), avian leukosis virus (ALV, avian C) and human foamy virus (HFV, spuma).

When the cell line is employed for packaging a retrovirus, the viral vector comprises long terminal repeat (LTR) sequences, the desired gene and a packaging sequence. Typically, therefore, the viral vector in such circumstances lacks functional gag, pol and env genes. These genes may be missing entirely or in part or be present but rendered non-functional. The viral vector thus generally comprises a retroviral genome lacking the appropriate functional genes but incorporating the gene of interest.

The desired gene is provided in the viral vector operably linked to a promoter. The gene may be a gene encoding a lymphokine or a cytokine. It may be a tumour suppressor gene, a corrective gene or a GDEPT (gene directed enzyme prodrug therapy) enzyme gene. The promoter may be a carcinoembryonic antigen (CEA), Muc-1, c-ErbB2, foliate binding protein (FBP) or vascular endothelial growth factor (VEGF) promoter. Termination sequences may be provided as required.

The viral vector is introduced into a cell line according to the invention which is provided with the viral functions that enable packaging/growth complementation to occur. Thus, the cell line is provided with the viral genes which are able to complement the functions of the viral vector. These genes express the viral proteins that enable packaging/growth complementation to occur, typically structural proteins, replicative enzymes and regulatory factors.

When the cell line is used for packaging a retrovirus, typically, the genes are the gag, pol and env genes. In particular, they are the functional viral genes that are missing from the viral vector.

The genes required by the cell line may be stably integrated into the cell genome. The genes may be provided in the form of proviral DNA. Any appropriate technique may be employed to introduce the genes into the cell line.

In use, a cell line harbouring the viral genes required for packaging is infected with a viral vector as above. The resulting packaged virus is then collected from the cell culture. The collected virus may be purified as desired prior to use in gene therapy.

Figure 2:
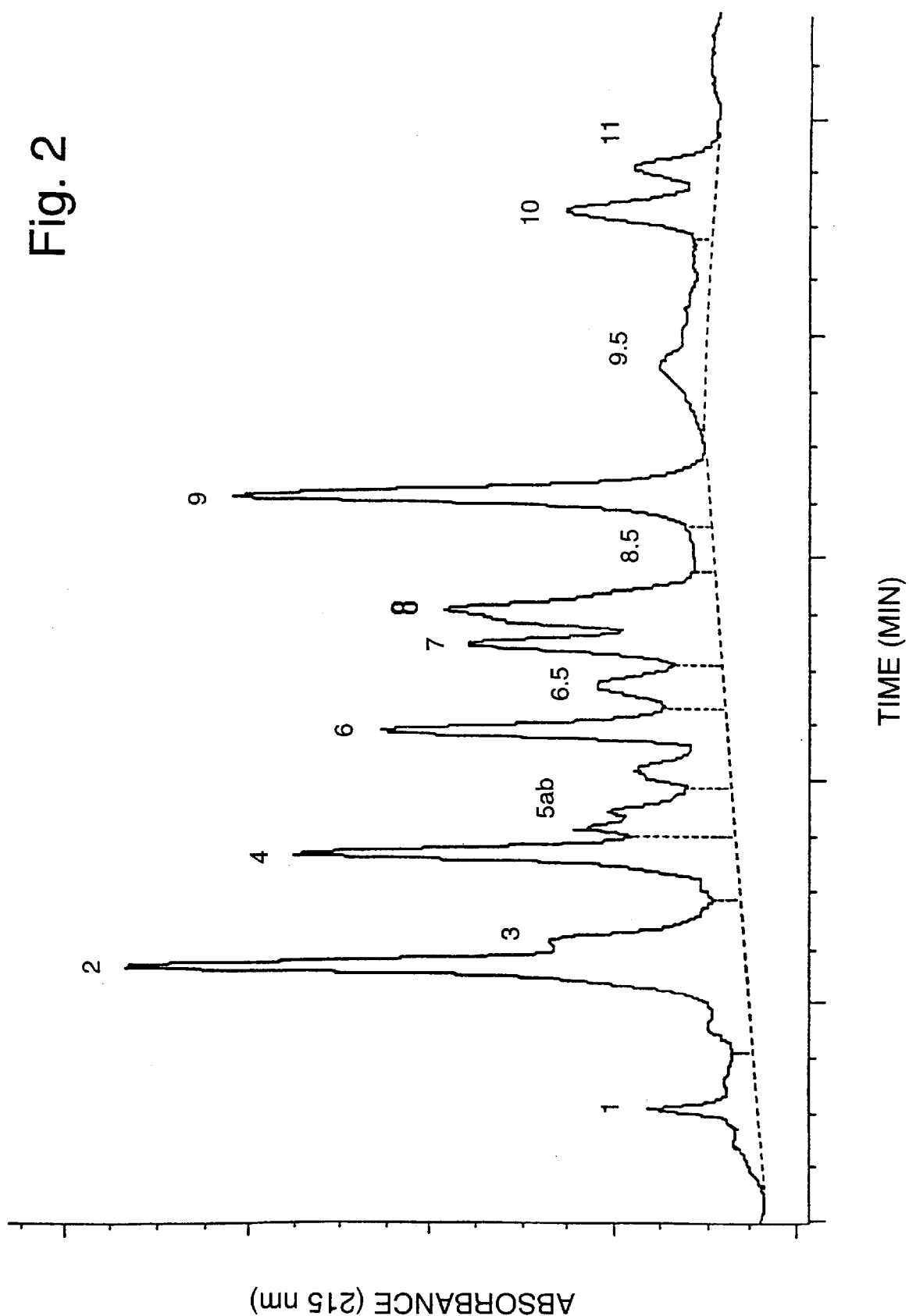

The following Examples illustrate the invention. In the accompanying drawings:

FIG. 1 shows the reversed phase high pressure liquid chromatography (RPHPLC) profile determined for the uncloned SMRV-positive Namalwa cell-line currently used in the production of Wellferon (Registered Trade Mark); and FIG. 2 shows the profile determined for the cloned SMRV-free Namalwa cell-line ECACC 94120841.

EXAMPLE 1

Testing of Namalwa Cell Line for the Presence of SMRV

1. General

A Namalwa cell line X which we located was tested for the presence of the SMRV genome. An assay procedure was adopted that used a genomic SMRV probe that will detect SMRV at less than 1 genome copy per cell and will routinely detect 1 genome copy per cell. Test DNA was cut with restriction endonucleases that yielded diagnostic-sized fragments that were detected by DNA hybridisation followed by autoradiography.

In addition, a polymerase chain reaction (PCR) assay was done using two SMRV/LTR specific oligonucleotide amplimers. Any amplified sequence would be identified by hybridisation with an oligonucleotide probe specific for SMRV. Under the conditions used, the procedure will detect at least 1 genome copy per 2000 cells or better. As the PCR assay was in fact negative, an additional assay employing nested primers within the SMRV genome was used. The nested primer set can detect SMRV to a sensitivity of 1 genome copy per 10,000 cells or better.

2. Methods (a) DNA Hybridisation

DNA Purification

A pellet consisting of approximately $7 \times 10^7$ test cells was used for DNA preparation. The cell pellet was resuspended in proteinase-K lysis buffer containing 20 $\mu$g ml$^{-1}$ RNase and 100 $\mu$g ml$^{-1}$ proteinase-K. The suspension was digested for 16 hours at 37° C. The deproteinised DNA was extracted twice with phenol and twice with phenol-chloroform and finally precipitated by ethanol in the presence of ammonium acetate. The DNA was recovered by centrifugation at 3000 g for 30 minutes and the supernatant discarded. The pellet was washed in 70% ethanol and allowed to air dry for 1 hour.

The DNA was allowed to redissolve in Tris EDTA (TE) buffer and the purity and concentration of the DNA was assessed by spectrophotometry. The absorbance was measured at 280 nm and 260 nm. The 260/280 ratio was 1.82 indicating that the sample DNA was pure. The yield of DNA was estimated to be 315 $\mu$g.

Control DNAs

The negative control DNA consisted of purified human placental DNA containing no detectable SMRV sequences.

The SMRV positive control DNA consisted of human placental DNA with added recombinant DNA, representing the complete SMRV genome, at 100, 10, 1 and 0.1 genome equivalents. Genome equivalents (g.e.) were calculated by assuming that the eukaryotic genome consists of $3 \times 10^9$ bp and the SMRV genome is $8.4 \times 10^3$ bp. In 10 $\mu$g of DNA one genome equivalent would be 28 pg of SMRV DNA.

Further positive controls consisted of Namalwa DNA known to harbour SMRV and CCL 194 DNA, a mink lung cell containing SMRV sequences at approximately 10 genome equivalents per cell.

The probe consisted of the full length SMRV genome isolated from the plasmid vector sequences.

(b) Preparation of DNAs for Hybridisation

10$\mu$g samples of test DNA, negative control human placental DNA, SMRV positive Namalwa DNA and CCL 194 DNA were digested to completion with the endonuclease BamHI, BglII, EcoRI and PstI. Recombinant positive controls were constructed by adding 100, 0.10, 1 and 0.1 genome equivalents of recombinant SMRV plasmid DNA to 10 $\mu$g human placental DNA. These were then digested to completion with the endonuclease EcoRI.

The resulting DNA fragments were separated by electrophoresis through an 0.8% agarose gel. The DNA was depurinated by a brief treatment with HCl, denatured in alkali and neutralized in situ before it was transferred to a charged nylon membrane by capillary blotting.

(c) Prehybridisation and Hybridisation

The membrane was prehybridised by incubating in hybridisation buffer containing 50% formamide in 4×SSPE at 42° C. for 2 hours.

After prehybridisation the buffer was replaced with fresh hybridization buffer containing denatured SMRV DNA labelled to a high specific activity with $^{32}$P.

The hybridisation was conducted for 16 hours at 42° C. Following hybridisation, the membrane was washed for 15 minutes at room temperature in 2×SSC/0.1% SDS, then for 15 minutes at 65° C. in 2×SSC/0.1% SDS followed by 3×30 minute washes at 65° C. in 0.1×SSC/0.1% SDS. Autoradiography of the membrane was performed by exposing it to X-ray film for 24 hours and 72 hours.

(d) Oligonucleotide Primers and Probes

Oligonucleotide Amplimers and Probe

Position on the SMRV genome: Amplimers encompassing the tRNA binding site were used: amplimer 1 is from nucleotide 805–825; amplimer 2 is from nucleotide 1006–990 and the probe is internal to oligonucleotide 863–888. The t-RNA binding site is from nucleotide 863–880.

Oligonucleotide Amplimers and Probe for Nested PCR

Position on the SMRV genome: for the outer primer set, amplimer 3 is from nucleotide 367–384 and amplimer 4 is from nucleotide 798–781. The inner primer set consists of amplimer 1 from nucleotide 401–421 and amplimer 2 from nucleotide 604–588. The probe is internal to the amplimers from nucleotide 459–482.

Internal Control Amplimers

The internal control amplimers used were from the β-globin gene and would amplify a DNA product of 205 bp.

(e) Sample Preparation

An aliquot of test cells were lysed by boiling in the presence of a matrix that efficiently absorbs lysis products that interfere with the PCR amplification process. The matrix was pelleted by microcentrifugation and the supernatant used for amplification. In all cases a positive displacement pipette was used which was designated for use with negative controls and test DNA only.

(f) Preparation of PCR Reactions

Sentinel Controls

Triplicate sentinel controls consisting of the SMRV reaction mix with no DNA were prepared before the preparation of test DNA and negative control samples. The tubes were left open for the duration of sample handling to assess possible contamination.

Negative Control Samples and Test Article Samples

Negative control samples consisted of duplicate human placental DNA equivalent to $2 \times 10^5$ cells (approximately 1 $\mu$g).

Test DNA samples consisted of duplicate partially purified DNA equivalent to $2 \times 10^5$ cells (approximately 1 $\mu$g).

Positive Controls

Aliquots of human placental DNA were spiked with a dilution of the SMRV genome equivalent to 1 copy in 500 cells (5.6 fg), 1 copy in 1000 cells (2.8 fg) and 1 copy in 2000 cells (1.4 fg). These aliquots were then added to the SMRV reaction mix. A further positive control consisting of 1 $\mu$g of purified CCL194 DNA was also added to the SMRV reaction mix.

β-Globin Internal Control

Triplicate sentinel controls consisting of β-globin reaction mix were prepared and aliquots of test DNA equivalent to 2×10⁵ cells were run in parallel with the SMRV reactions to ensure the DNA was able to be amplified.

(g) Preparation of Nested PCR Reactions

Primary (Outer) Reactions

Triplicate sentinel controls consisting of the primary (outer) SMRV reaction mix with no DNA were prepared before the preparation of test DNA and negative control samples. The tubes were left open for the duration of sample handling to assess possible contamination.

Negative control samples consisted of duplicate human placental DNA equivalent to 2×10⁵ cells (approximately 1 μg).

Test DNA samples consisted of duplicate partially purified DNA equivalent to 2×10⁵ cells (approximately 1 μg).

Aliquots of human placental DNA were spiked with a dilution of the SMRV genome equivalent to 1 copy in 500 cells (5.6 fg), 1 copy in 1000 cells (2.7 fg) and 1 copy in 2000 cells (1.4 fg). These aliquots were then added to the reaction mix. A further positive control consisting of 1 μg of purified CCL 194 DNA was also added to primary (outer) SMRV reaction mix.

Secondary (Inner) Nested Reactions

After the first round of PCR (Primary) was finished, 2 μl (1/20) of each reaction was removed and added to secondary (inner) SMRV reaction mix.

(h) PCR Reaction Conditions

The reaction conditions for PCR were as follows: β-globin and SMRV PCR:3 cycles consisting of denaturation at 97° C. for 1 minute, annealing at 55° C. for 45 seconds and extension at 68° C. for 1 minute. This was followed by 30 cycles consisting of denaturation at 95° C. for 1 minute, annealing at 55° C. for 45 seconds and extension at 68° C. for 1 minute. A final extension of the DNA was done for 10 minutes at 68° C. after cycling.

The reaction conditions for PCR with nested primers were as follows:

First Reaction 2 cycles consisting of denaturation at 95° C. for 3 min., annealing to 55° C. for 45 seconds and extension at 72° C. for 2 minutes. This was followed by 25 cycles consisting of denaturation at 95° C. for 1 minute, annealing at 55° C. for 45 seconds and extension at 68° C. for 1 minute.

Second Reaction 3 cycles consisting of denaturation at 97° C. for 1 minute, annealing at 55° C. for 45 seconds and extension at 68° C. for 1 minute. This was followed by 30 cycles consisting of denaturation at 95° C. for 1 minute annealing at 55° C. for 45 seconds and extension at 68° C. for 1 minute. A final extension of the DNA was done for 10 minutes at 68° C. after cycling.

(i) Electrophoresis and Hybridisation

Aliquots of the finished reactions were electrophoresed through a 5% (v/v) acrylamide gel (SMRV PCR products) or a 1.5% agarose gel (nested PCR products), stained in ethidium bromide and examined and photographed under UV light. The DNA was denatured, neutralised in situ and transferred to charged nylon membranes by electroblotting (SMRV PCR products) or by capillary blotting (nested PCR products). The DNA was bound to the membranes by baking at 80° C.

The membranes were pre-hybridised by incubation in hybridisation buffer containing 5×SSC, and 7% SDS (w/v) at 50° C. for 2 h. After pre-hybridisation the buffer was replaced with hybridisation buffer containing a $^{32}$P-5'-end labelled oligonucleotide specific for SMRV. The hybridisation was continued for 16 h at 50° C. Following hybridisation the membranes were washed for 3×2 minutes in 5×SSC/0.1% SDS (w/v) at ambient temperature followed by 3×30 minutes washes in 5×SSC/0.1 SDS (w/v) at 50° C. and a final wash of 5 minutes at 68° C. (Tm-4° C.). Autoradiography of the membrane was performed by exposing the filters to X-ray film for 16 h.

2. Validity and Results (a) Validity

DNA Hybridisation

Under the hybridisation conditions used, the SMRV probe detected down to one genome equivalent of SMRV in a background of virus-negative human placental DNA. Sensitivity of detection for the virus would be of the order of 0.1 g.e. per cell.

PCR

A valid test is defined as a test where appropriate amplification of the target sequences is detected in the positive control DNA and absent for all the negative controls. In addition, amplification of a genomic target sequence must be seen in all samples. The test was valid: amplification of the target sequences was detected in the positive control DNA and was absent in the negative controls. Amplification of the β-globin genomic target was detected in all the samples.

(b) Test Results: DNA Hybridisation

Absence of SMRV specific sequences in the test DNA: there was no hybridisation of the radiolabelled SMRV probe to the negative control DNA or the test DNA under stringent conditions of hybridisation.

(c) Test Results PCR

β-Globin Internal Control

Analysis of the triplicate sentinel controls showed no visible amplified bands. However, each reaction mix containing DNA displayed a discrete band of the expected size of approximately 205 bp thereby indicating that the DNA was suitable for PCR amplification.

Negative Controls

No amplified DNA fragments could be seen in the three sentinel controls or the negative control DNA reactions. No specific hybridisation of the radiolabelled probe to either the sentinel controls or the negative control DNA was detected.

Positive Controls

The expected size of the amplified fragment from SMRV DNA would be 201 bp (from nucleotide 805–1006). A discrete band of approximately 201 bp was detected in the three recombinant positive control DNA lanes containing 56 fg, 2.8 fg and 1.4 fg amounts of SMRV DNA and in the CCL 194 positive control lane. This 201 bp was detected by the radiolabelled probe indicating that the reactions had amplified the expected fragments. The sensitivity of the assay is of the order of 1 g.e. in 2000 cells.

Test DNA

No specific amplified DNA fragments were detected in the test DNAs either visually or following hybridisation with the radiolabelled probe.

(d) Test Results Nested PCR, Secondary (Internal) Reactions

Negative Controls

No amplified DNA fragments could be seen in the three sentinel controls or the negative control DNA reactions. No specific hybridisation of the radiolabelled probe to either the sentinel controls or the negative control DNA was detected.

Positive Control

The expected size of the amplified fragment from SMRV DNA would be 203 bp (from nucleotide 401–604). A discrete band of approximately 203 bp was detected in the three recombinant positive control DNA lanes containing 5.6 fg, 2.8 fg and 1.4 fg amounts of SMRV DNA and in the CCL 194 positive control lane. This 203 bp band was detected by the radiolabelled probe indicating that the reactions had amplified the expected fragments. The band was detected in positive controls containing 1.4 fg, 0.7 fg, 0.35 fg, 0.175 fg and 0.087 fg dilutions of DNA. These samples were not subjected to DNA hybridisation analysis. The sensitivity of the assay is less than 1 g.e. in 10,000 cells.

Test DNA

No specific amplified DNA fragments were detected in the test DNAs either visually or following hybridisation with the radiolabelled probe.

3. Conclusion

The results are consistent with both the negative control human placental DNA and the test DNA from Namalwa cell line X being free of SMRV.

EXAMPLE 2

SMRV negative Namalwa cells were cloned by double limiting dilution to achieve a 99.99% statistical probability that the derived clone was generated from a single cell. Parental cells from Namalwa cell line X were grown in static culture in a medium comprising RPMI 1640 medium supplemented to 10% foetal bovine serum, 100 Uml$^{-1}$ penicillin, 100 $\mu$gml$^{-1}$ streptomycin and 4 mM glutamine. The cells were grown in static culture and split every 2–3 days; diluting in growth medium down to 0.2 million cells ml$^{-1}$ and maintaining only cultures demonstrating >90% viability as indicated by trypan blue exclusion.

Only cells showing growth of 0.2 to 2 million cells ml$^{-1}$ in a three day period were selected for dilution cloning and it was found to be essential that dilution cloning was carried out on cells which had grown to a density of about 2 million cells ml$^{-1}$. Selected cells were diluted into 96-well low-evaporation trays; plating out at between 1 and 300 cells/well grown for three weeks, wrapped in aluminium foil.

Single colonies were picked from plates having less than 10% of wells with single colonies and subjected to a second round of dilution cloning. Double diluted clones were then compared by small scale IFN induction using a cell concentration of 1 million cells ml$^{-1}$ in 12-well trays, treating with 1 mM sodium butyrate and then adding 1 $\mu$l of Sendai virus per well. IFN was harvested after a further 24 hours and assayed by ELISA. Those clones for which ELISA indicated a satisfactory quantitative expression of IFN were further amplified in larger scale cultures/inductions and subjected to qualitative analysis of a $\alpha$-IFN subunit profile by reversed phase high pressure liquid chromatography (RPHPLC) to select those clones A, B, C, D, etc displaying the desired profile.

EXAMPLE 3

$\alpha$-IFN produced and purified in accordance with standard manufacturing practice (Lewis, W. G. and Finter, N. B. (1987), "The Production and Purity of a mixed human alpha interferon preparation (Wellferon) derived from lymphoblastoid cells" in *The Interferon System* (Eds. Baron, S., Dianzani, F., Stanton, G. J. and Fleischmann, W. R. Jnr). Texas University Press) was analysed for RPHPLC generated subtype profile and as illustrated in FIG. 1.

EXAMPLE 4

Purification Protocol for Interferon Produced by Cloned Namalwa Cells Deposit Accession No. ECACC 94120841

A SMRV-negative clone was selected, ECACC 94120841, and was grown in 3×300 ml shake flasks, and induced with Sendai virus after butyrate treatment according to standard protocols (Lewis, W. G. and Finter, N. B., supra). The culture supernatant was harvested and purified by two passes on a purified anti-interferon antibody immunoaffinity column. The interferon was concentrated and analysed by RPHPLC to determine the subtype composition which is illustrated in Table 2 and the profile which is shown in FIG. 2. It must be noted that the purity of the interferon achieved in a small scale laboratory preparation was not comparable to that of a production batch of interferon (Example 2 and FIG. 1) and therefore the values for peak are percent shown below may be influenced by the presence of non-interferon protein.

TABLE 2

| Peak | α-IFN subtype | Peak area % | Acceptable range |
| --- | --- | --- | --- |
| 1 | 14 | 5 | 2–13 |
| 2 + 3 | 2b | 24 | 19–37 |
| 4 | 21 | 11 | 8–20 |
| 5 | 5 | 6 | 4–13 |
| 6 | 10 | 11 | 8–21 |
| 7 + 8 | 7 + 17 | 15 | 11–20 |
| 9 | 8 | 11 | 2–14 |
| 10 + 11 | 1 | 7 | 1–16 |

Table 2 shows the RPHPLC elution peak number with the corresponding $\alpha$-IFN sub-type and the relative proportion ("Peak Area %") of each sub-type obtained from the cloned cell-line together with, for comparison, the range of each sub-type in therapeutically acceptable lymphoblastoid interferon.

By comparing FIGS. 1 and 2, a highly significant and sufficient level of identity can be seen between the IFN profiles for the SMRV-positive Namalwa cell line currently used for the production of Wellferon (Registered Trade Mark) (FIG. 1) and the SMRV-negative Namalwa cell line ECACC 94120841. The interferon derived from the cell-lines can be considered to be substantially equivalent.

All references to $\alpha$-IFN sub-types herein are consistent with the nomenclature of human interferon proteins approved by the International Society for Interferon and Cytokine Research and published in the Journal of Inteferon Research 14:223–226 (1994).

We claim:

1. A Namalwa cell line which is free of squirrel monkey retrovirus.

2. A cell line according to claim 1 which produces a population of alpha-interferon sub-types comprising sub-types 2b, 7, 10, 17 and 21.

3. A cell line according to claim 2 wherein the sub-types comprise sub-types 1, 2b, 5, 7, 8, 10, 14, 17 and 21.

4. A cell line according to claim 3, wherein the alpha-interferon sub-type 1 is produced in an amount of 1–16% by weight, the alpha-interferon sub-type 2b is produced in an amount of 19–37% by weight, the alpha-interferon sub-type 5 is produced in an amount of 4–13% by weight, the alpha-interferon sub-type 7+17 is produced in an amount of 11–20% by weight, the alpha-interferon sub-type 8 is produced in an amount of 2–14% by weight, the alpha-interferon sub-type 10 is produced in an amount of 8–21% by weight, the alpha-interferon sub-type 14 is produced in an amount of 2–13% by weight, and the alpha-interferon sub-type 21 is produced in an amount of 8–20% by weight.

5. A cell line according to claim 1 which produces a population of alpha-interferon sub-types which are the same as those produced by cell line ECACC 94120840 or ECACC 94120841.

6. A cell line according to claim 5 wherein the population of sub-types is substantially the same as that produced by cell line ECACC 94120840 or ECACC 94120841.

7. A cell line according to claim 1 which is free of squirrel monkey retrovirus and is cell line ECACC 94120840 or ECACC 94120841 or the progeny of either.

8. A cell line according to claim 1 which harbours an exogenous expressible DNA sequence encoding a polypeptide of interest.

9. A cell line according to claim 1 which harbours sufficient expressible viral genes to enable a corresponding viral vector comprising replication signals, a packaging sequence and a gene of interest to be packaged therein.

10. A process for the preparation of alpha-interferon, which process comprises culturing a cell line as defined in claim 1 and isolating the alpha-interferon thus produced.

11. A process for the preparation of a cell line as defined in claim 8, which process comprises transfecting a cell line as defined in claim 1 with an expressible DNA sequence encoding the polypeptide of interest.

12. A process for the preparation of a polypeptide of interest, which process comprises maintaining a cell line as defined in claim 8 under such conditions that the said polypeptide is expressed and recovering the expressed polypeptide.

13. A process for the preparation of a cell line as defined in claim 9, which process comprises transfecting a Namalwa cell line which is free of squirrel monkey retrovirus with sufficient expressible viral genes to enable a corresponding viral vector comprising replication signals, a packaging sequence and a gene of interest to be packaged therein.

14. A process for packaging viruses, which process comprises transfecting a cell line as defined in claim 9 with a corresponding viral vector comprising replication signals, a packaging sequence and a gene of interest and recovering the resulting packaged virus.

* * * * *